United States Patent
Chumanov et al.

(12)

(10) Patent No.: US 9,023,295 B2
(45) Date of Patent: May 5, 2015

(54) ADAPTER FOR HAND-HELD ELECTRONIC DEVICES FOR USE IN DETECTING OPTICAL PROPERTIES OF SAMPLES

(71) Applicants: Rob Chumanov, Middleton, WI (US); Julia Krueger, Fitchburg, WI (US); Steve Krueger, Fitchburg, WI (US); Sydnor T. Withers, III, Madison, WI (US)

(72) Inventors: Rob Chumanov, Middleton, WI (US); Julia Krueger, Fitchburg, WI (US); Steve Krueger, Fitchburg, WI (US); Sydnor T. Withers, III, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 13/705,764

(22) Filed: Dec. 5, 2012

(65) Prior Publication Data

US 2014/0154152 A1    Jun. 5, 2014

(51) Int. Cl.
| | |
|---|---|
| *G01N 21/00* | (2006.01) |
| *B01L 9/00* | (2006.01) |
| *H04M 1/00* | (2006.01) |
| *H04M 1/02* | (2006.01) |
| *G01J 3/02* | (2006.01) |

(Continued)

(52) U.S. Cl.
CPC ............... *B01L 9/00* (2013.01); *H04M 1/0202* (2013.01); *G01J 3/0291* (2013.01);

(Continued)

(58) Field of Classification Search
None
See application file for complete search history.

(56) References Cited

U.S. PATENT DOCUMENTS

| | | | | |
|---|---|---|---|---|
| 6,159,424 A | * | 12/2000 | Kauhaniemi et al. | ............ 422/63 |
| 2005/0201898 A1 | * | 9/2005 | Borich et al. | ............... 422/82.05 |
| 2006/0222567 A1 | | 10/2006 | Kloepfer et al. | |

FOREIGN PATENT DOCUMENTS

| | | |
|---|---|---|
| GB | 2474701 A | 4/2011 |
| GB | 2483482 A | 3/2012 |

OTHER PUBLICATIONS

Dasheng Lee, Wen Pin Chou, Shiou Hwei Yeh, Pei Jer Chen, Ping Hei Chen, DNA Detection Using Commercial Mobile Phones, Biosensors and Bioelectronics, May 5, 2011, 4349-4354, 26 (2011), Elsevier B.V.

(Continued)

*Primary Examiner* — Neil N Turk
(74) *Attorney, Agent, or Firm* — McAndrews, Held & Malloy, Ltd.

(57) ABSTRACT

An adapter for use with a hand-held electronic device for use in detecting the optical properties of a sample. The adapter includes a backing plate having an integral surface that secures the adapter to the electronic device. The adapter also includes a sample housing having a sample holder and a cap. The sample holder is configured to receive the placement of a sample and/or a sample vessel. The backing plate includes an orifice that allows the passage of light from the sample to the detector of the electronic device. The backing plate may also include another orifice that allows for light emitted from an emitter of the electronic device to enter into the sample holder. The sample holder may also include reflective surfaces that direct light to/from the sample as well as filters that filter the wavelength of light sent to sample and/or detected by the detector.

12 Claims, 15 Drawing Sheets

(51) Int. Cl.
- *G01N 21/01* (2006.01)
- *G01N 21/25* (2006.01)
- *G02B 13/00* (2006.01)
- *G01N 21/64* (2006.01)
- *G01N 21/76* (2006.01)
- *G02B 21/00* (2006.01)
- *G01J 3/51* (2006.01)
- *G01N 15/06* (2006.01)
- *A61B 5/00* (2006.01)
- *G01N 21/03* (2006.01)
- *G02B 21/34* (2006.01)

(52) U.S. Cl.
CPC .............. *A61B 5/6898* (2013.01); *G01J 3/0202* (2013.01); *G01N 21/01* (2013.01); *G01N 21/255* (2013.01); *G02B 13/001* (2013.01); *G01N 21/6456* (2013.01); *G01N 21/76* (2013.01); *G01N 2021/0143* (2013.01); *G01N 2021/0367* (2013.01); *G01N 2021/6482* (2013.01); *G01N 2201/0221* (2013.01); *G01J 3/0272* (2013.01); *G02B 21/0008* (2013.01); *G02B 21/34* (2013.01); *G01J 3/513* (2013.01); *A61B 5/0059* (2013.01)

(56) References Cited

OTHER PUBLICATIONS

PCT, Notification of Transmittal of the International Search Report and the Written Opinion of the International Searching Authority, or the Declaration, in Application No. PCT/US2013/071838, dated Feb. 20, 2014. (15 pages).

* cited by examiner

ADAPTER FOR HAND-HELD ELECTRONIC DEVICES FOR USE IN DETECTING OPTICAL PROPERTIES OF SAMPLES

BACKGROUND OF THE INVENTION

Certain embodiments of the present invention generally relate to an adapter used in connection with detecting the optical properties of a physical sample(s), such as, for example, blood samples or other physical specimens. More specifically, certain embodiments of the present invention relate to an adapter for use with hand-held electronic devices, the adapter being configured to hold a sample(s) or a sample vessel containing the sample(s), so that the detector of the device may detect light, an image, and/or other data corresponding to an optical property of the sample.

Systems used to test the properties of samples often involve adding one or more reagents to the sample that may react and/or bind to the sample. The resulting reaction and/or binding of the reagents with/to the sample may then be indicated through the detection or measuring of one or more optical properties of the sample. Such optical properties may provide information that may be used to determine one or more properties of the sample, such as, for example, the presence of certain components, chemicals, or chemical structures in the sample, among other properties.

A variety of different types of detection devices may be used to detect optical properties of a sample(s). For example, the luminescence of a sample may be measured through the use of a luminometer. More specifically, a luminometer may measure the light emitted by, or through, the sample. The resulting level of detected light may provide an indication of one or more properties, or the contents, of the sample. Alternatively, the optical properties of a sample may be measured by a fluorometer, which may detect the wavelength of the light that is emitted by, from, and/or through a sample. Moreover, certain chemicals and chemical structures in a sample may be excited as they absorb light of one wavelength and will emit light at a different wavelength. The wavelength of the light emitted by the sample that is detected by the fluorometer may also provide an indication of the presence of a particular chemical(s) or chemical structure(s) in the sample.

The amount of light that a sample absorbs as light passes through the sample may also be measured in evaluating the properties of the sample. Such detection may involve the detector measuring the light that passes through the sample, which may then be used as an indication of the quantity of light that the sample absorbed. Such detection may, in at least some instances, also employ the use of one or more filters that filter out a particular or defined wavelength(s) of light that is sent to the sample and/or detected by the detector. Further, the wavelength selected for filtering may also depend on the type of light being filtered, such as whether the light is excitation light from a light source or emission light that is released from the sample. For example, a filter may be used for excitation light having wavelengths of 504 nm, while a filter for emission light may be used for wavelengths of 532 nm, among others. However, a wide range of filters for different wavelengths of light may be selected.

Additionally, the color of the sample may be detected or measured. More specifically, a sample may, or may not, undergo a change in color when the sample reacts with the reagent(s) or when the reagent(s) binds to the sample. Therefore, the color of the sample may also be used in determining the presence of a compound, chemical, or chemical structure in the sample.

In many of these applications, it is possible to perform more than one of the above-identified detections or measurements simultaneously using a single device, commonly referred to as multiplexing. Such multiplexing may require that the measuring equipment employ multiple filters that are either used simultaneously, or changed, for the different measurements.

Such detection or measurement equipment, however, is typically specialized in that the equipment generally has limited use outside of measuring optical properties of samples. Accordingly, unless there is an anticipated use for the equipment, the equipment is generally not in the possession of, or carried with, a technician. Accordingly, when a technician is away from a lab or facility where the equipment is often used and/or stored, the technician may not have access to the necessary equipment. Further, given the generally specialized and dedicated nature of such testing equipment, in some situations, ownership of the equipment is not worth its expense, which may then require that the samples be sent to a facility having the necessary measuring equipment, thereby delaying the speed at which desired information regarding the sample is obtained.

Unlike equipment traditionally used to measure the optical properties of samples, hand-held consumer electronic devices, such as, for example, smart phones and tablets, among others, are often carried by individuals both at and away from the work place. Such hand-held devices often include a wide array of functional components that are controlled by programmable microprocessors or computers to perform a number of different tasks using the device's existing operating system(s). For example, smart mobile telephones may include a camera and an associated program(s) that allow the telephone to read UPC barcodes. Additionally, such hand-held consumer electronic devices may include processor-based applications that allow for the determination of the location of the device through the use of global positioning system (GPS) coordinates.

Hand-held electronic devices are also often connectable to a network to allow for the transfer and/or distribution of data collected and/or derived by, or through operation of, the device. Such networking capabilities often allow for data collected by the device to be transferred from the device to the network. This data transfer may be used for a variety of different purposes, including modifying information displayed, stored, or otherwise provided by the network and/or maintained and displayed by certain websites. In some applications, such data transfer from the device to the network may occur, for example, by a wireless connection between the device and the network or component thereof, by operably connecting the data port of the device to a data cable or docking station that is connected or linked to the network or otherwise downloading the data to a memory device that allows for the transfer of the data to the network among other forms of data transfer.

BRIEF SUMMARY OF THE INVENTION

An aspect of the invention is an adapter for use with a hand-held consumer electronic device, the hand-held consumer electronic device having a detector and an imaging device for detecting one or more properties of a sample. The adapter includes a backing plate having at least one orifice and at least one integral surface. The at least one integral surface is configured to engage at least a portion of an outer surface of the hand-held consumer electronic device to secure the adapter to the hand-held consumer electronic device. Additionally, at least one of the at least one orifices is positioned along the backing plate so as to generally align with the detector when the adapter is secured to the hand-held consumer electronic device. The adapter also includes a sample holder that is operably secured to the backing plate. The sample holder includes an aperture and a chamber. The aperture is in communication with at least a portion of a chamber. The chamber is configured to receive the placement of at least a portion of the sample or the sample vessel. Additionally, the aperture is generally aligned with the detector and at least one of the at least one orifice when the backing plate is secured to the hand-held consumer electronic device. The adapter further includes a cap that is configured to engage the sample holder. The cap is configured to cover at least a portion of the chamber or the sample vessel when the cap is engaged in a closed position with the sample holder.

Another aspect of the invention is an adapter for use with a hand-held consumer electronic device, the hand-held consumer electronic device having a detector and a light emitter for detecting one or more properties of a sample. The adapter includes a backing plate configured to be adjacent to an outer surface of the hand-held consumer electronic device when the adapter is secured to the device. The backing plate includes a first orifice, a second orifice, and at least one integral surface. The at least one integral surface is configured to engage an outer surface of the hand-held consumer electronic device to secure the adapter to the consumer electronic device. Further, the first orifice is positioned to generally align with the detector, and the second orifice is positioned to generally align with the light emitter, when the adapter is secured to the hand-held consumer electronic device. The adapter also includes a sample holder that is operably secured to the backing plate. The sample holder includes a first reflective surface, a second reflective surface, and a chamber. The first reflective surface is configured to reflect at least a portion of the light emitted from the light emitter toward a portion of the chamber. The second reflective surface is configured to reflect at least a portion of the light that passes out of the chamber to the detector. A cap is configured to engage the sample holder, with the cap being configured to cover at least a portion of the chamber or the sample vessel when the cap is engaged in a closed position with the sample holder.

A further aspect of the invention is an adapter for use with a hand-held consumer electronic device, the hand-held consumer electronic device including a detector and a light emitter used in detecting one or more optical properties of a sample.

The adapter includes a backing plate having a first side, a second side, an orifice, and at least one integral surface. The at least one integral surface is configured to engage a portion of the outer surface of the hand-held consumer electronic device to secure the adapter to the consumer electronic device. Further, the orifice is positioned along the backing plate so as to generally align with the detector when the adapter is secured to the hand-held consumer electronic device. Additionally, the adapter includes a sample holder that is operably secured to the second side of the backing plate. The sample holder includes a first reflective surface, a chamber wall, a first aperture, and a second aperture. The first and second apertures are separated by a divider. Further, the chamber wall defines a chamber that is configured to receive the insertion of the sample or a sample vessel. The first reflective surface is positioned to reflect a portion of a light emitted from the light emitter toward an orifice in the divider and into a portion of the chamber. The chamber wall also includes an orifice that is positioned to allow light to pass from the sample, through the first aperture and the orifice of the backing plate, and to the detector. The adapter also includes a cap that is configured to engage the sample holder and to cover at least a portion of the chamber or sample vessel when the cap engages the sample holder in a closed position.

Figure 1:
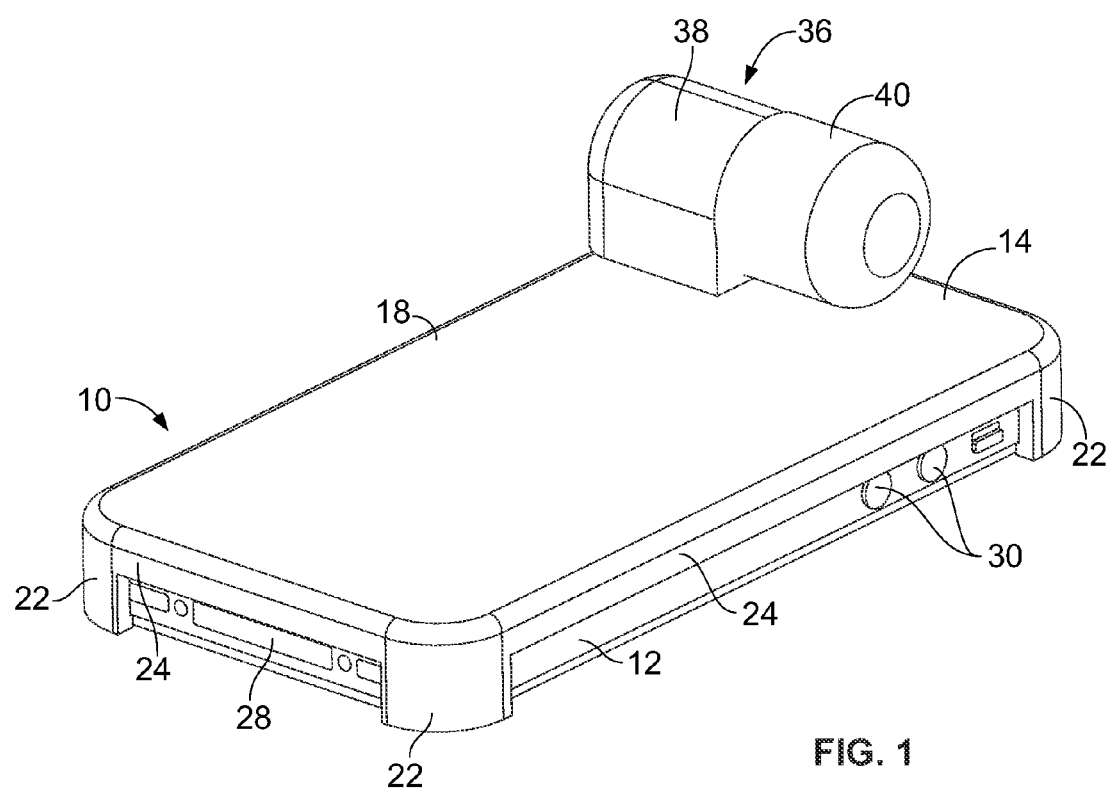
FIG. 1 illustrates a perspective view of an adapter secured to a hand-held electronic device that is used to detect an optical property of a sample, according to an embodiment of the present invention.

The foregoing summary, as well as the following detailed description of certain embodiments, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

The following reference characters are used in the specification and figures:

| | |
|---|---|
| 10 | Adapter |
| 12 | Hand-held electronic device |
| 13 | Back surface |
| 14 | Backing plate |
| 16 | First side |
| 18 | Second side |

-continued

| | |
|---|---|
| 20 | Orifice |
| 21 | Second orifice |
| 22 | Integral surface |
| 24 | Edge (of adapter 10) |
| 26 | Edge (of hand held electronic device 12) |
| 28 | Data port |
| 30 | Button |
| 32 | Detector |
| 34 | Light emitter |
| 35 | Seal |
| 36 | Sample housing |
| 38 | Sample holder |
| 40 | Cap |
| 42 | Chamber |
| 43 | Chamber wall |
| 44 | Sample vessel |
| 46 | Aperture |
| 48 | Projection (of backing plate 14) |
| 50 | Recess (of sample holder 38) |
| 52 | Protrusion |
| 53 | Depression |
| 54 | Cavity |
| 56 | Extender |
| 57 | Passage |
| 58 | Recess (of extender 56) |
| 59 | Outer surface |
| 60 | Filter (for first orifice 20) |
| 62 | Filter (for second orifice 21) |
| 63 | Hub |
| 64 | Hub |
| 70 | Adapter |
| 72 | Sample housing |
| 73 | Wall |
| 74 | Sample holder |
| 75 | Aperture |
| 76 | Upper portion |
| 78 | Divider |
| 80 | Reflective surface |
| 81 | Insert |
| 82 | Window |
| 84 | Opening |
| 90 | Adapter |
| 92 | Sample housing |
| 93 | Wall |
| 94 | Sample holder |
| 96 | Aperture |
| 98 | Distal end |
| 100 | Divider |
| 102 | Orifice (in divider 100) |
| 104 | Orifice (in chamber wall 43) |

DETAILED DESCRIPTION OF THE INVENTION

The present invention will now be described more fully with reference to the accompanying drawings, in which several embodiments are shown. This invention may, however, be embodied in many different forms and should not be construed as limited to the embodiments set forth here. Rather, these certain embodiments are examples of the invention, which has the full scope indicated by the language of the claims. Like numbers refer to like elements throughout.

Figure 2:
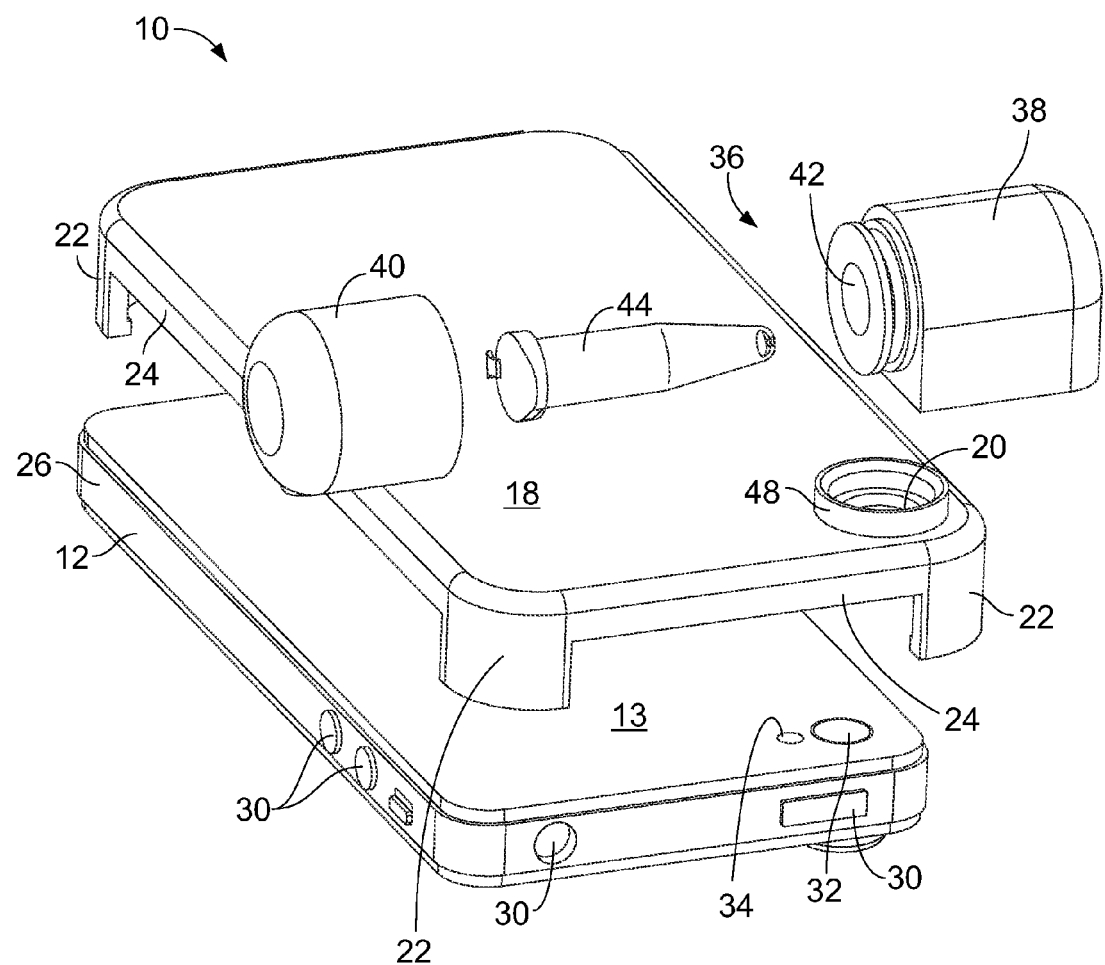
FIG. 2 illustrates a rear exploded view of the adapter and the hand-held electronic device shown in FIG. 1.
Figure 3:
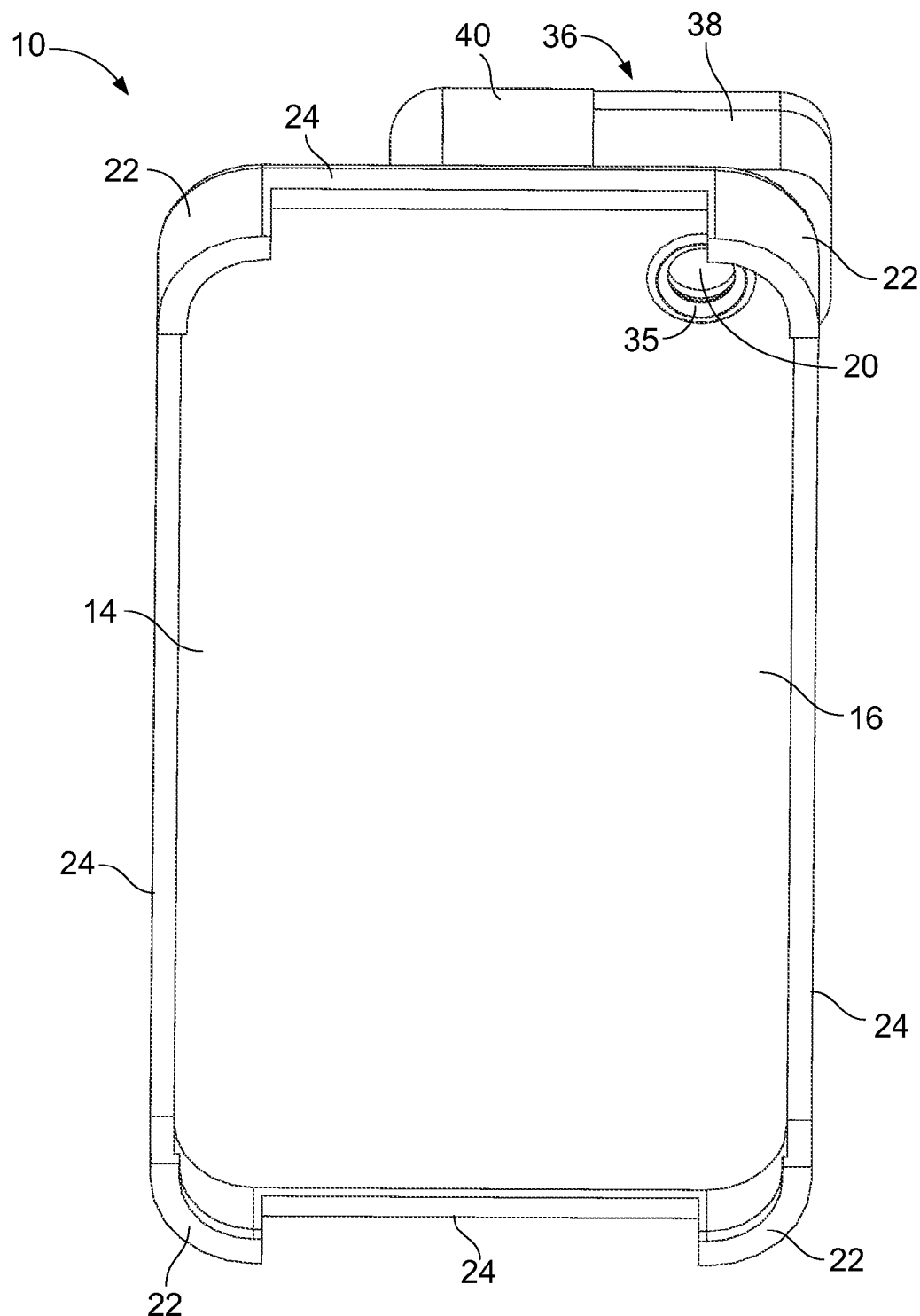
FIG. 3 illustrates a front perspective view of an adapter shown in FIG. 1.

FIGS. 1 and 2 illustrate an adapter 10 and a hand-held electronic device 12 that are used in detecting an optical property of a sample, according to an embodiment of the present invention. FIG. 3 illustrates a front side perspective view of the adapter 10. As shown, the adapter 10 includes a backing plate 14 that has a first side 16, a second side 18, and at least one orifice 20. The backing plate 14 also includes at least one integral surface 22 that is used to secure the adapter 10 to the hand-held electronic device 12. For example, as shown in FIGS. 1-4 in the illustrated embodiments, the at least one integral surface 22 includes four arms or tabs that extend or project away from an edge 24 and/or the first side 16 of the backing plate 14. These four integral surfaces 22 are configured to engage an outer surface of the device 12, such as, for example, an edge 26 of the device 12. Moreover, the integral surfaces 22 may, for example, provide a friction or snap fit with the edge 26 that secures the adapter 10 to the device 12. In the illustrated embodiment, when adapter 10 is secured to the device 12, the first side 16 of the backing plate 14 is adjacent to and/or abuts against at least a portion of the electronic device 12.

While FIGS. 1-4 illustrate the integral surface 22 as being four arms or tabs, the integral surface may take a variety of different shapes, orientations, or configurations. For example, according to certain embodiments, the integral surface 22 may extend from areas of the adapter 10 in which the integral surface 22 will not engage the corner area of the device 12, but instead are located at one or more intermittent and/or intermediate locations along the edges 26 of the device 12, such as at locations along the edges 26 that are between the corners of the device 12. Further, a different number of integral surfaces 22 may be employed, such as two integral surfaces 22 on opposing sides 24 of the adapter 10. Alternatively, the adapter may include a single integral surface 22 that is configured to extend along at least a portion of two or more edges 26 of the device 12. The length of each of the integral surface 22 may also vary from what is shown in FIGS. 1-4. Additionally, the adapter 10 may include multiple integral surfaces 22 that have two or more different lengths. For example, the integral surfaces 22 that engage opposing left and right edges 26 of the device 12 may be longer than the integral surfaces that engage opposing top and bottom edges 26 of the device 12. Further, according to certain embodiments, the integral surface 22 may have one or more orifices that permit access to a data port 28 or a button(s) 30 of the hand-held electronic device 12 when the adapter 10 is secured to the device 12.

Figure 4:
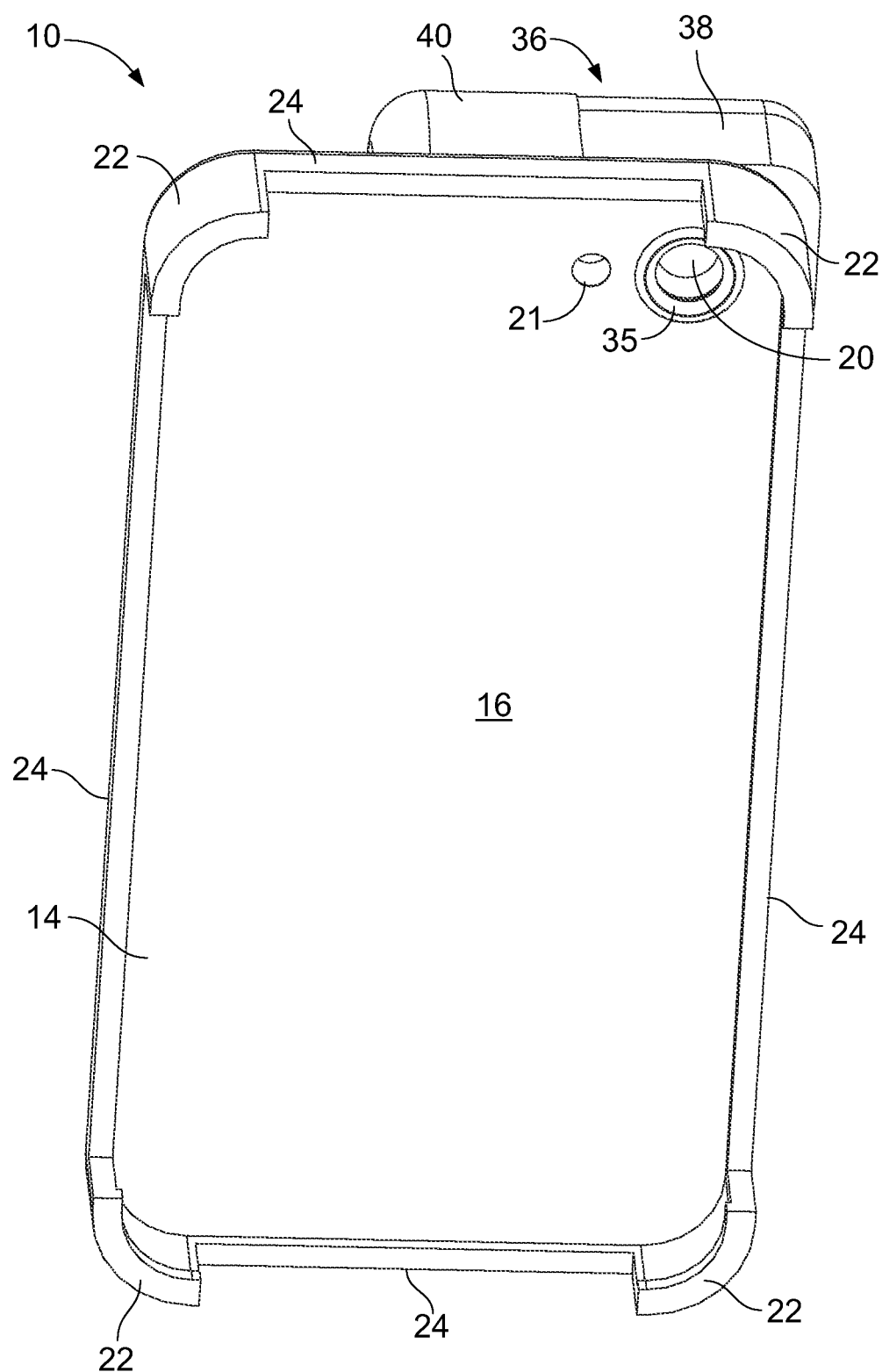
FIG. 4 illustrates a front perspective view of the adapter having a first and second orifice in the backing plate, according to an embodiment of the present invention.

Referencing FIGS. 2 and 3, the adapter 10 includes at least one orifice 20 in the backing plate 14. The orifice 20, also referred to as the first orifice 20, is positioned such that, when the adapter 10 is secured to the hand-held electronic device 12, the orifice 20 is generally aligned with a detector 32 of the hand-held electronic device 12. According to such embodiments, the detector 32 may be a lens and/or optical portion of a digital camera. Such alignment may allow for light to pass directly or indirectly through/from a sample in the adapter 10 to the detector 32. Additionally, as shown in FIG. 4, according to certain embodiments, the backing plate 14 may have a first orifice 20 and a second orifice 21, the second orifice 21 being generally aligned with a light emitter 34 of the hand held electronic device 12, such as a light emitting diode. The light emitter may provide a light that induces an optical property from/in the sample that is subsequently detected by the detector 32.

Alternatively, the first orifice 20 may be configured to be large enough to provide a passage in the backing plate 14 for the travel of light both from the light emitter 34 as well as light to the detector 32. According to certain embodiments, a seal 35, such as an O-ring may be positioned between the orifice 20 and the detector 32 so as to assist in preventing the detector 32 from detecting light that passes between the first side 16 of the backing plate 14 and a back surface 13 of the device 12.

Referencing FIGS. 1-5, the adapter 10 also includes a sample housing 36 having a sample holder 38 and a cap 40. The sample holder 38 includes a chamber wall 43 that at least partially defines a chamber 42. The chamber 42 is configured to receive the placement of a sample and/or a sample vessel 44 that contains the sample. The sample holder 38 also includes at least one aperture 46. According to certain embodiments, the sample holder 38 contains at least one aperture 46 that is in communication with at least a portion of the chamber 42 and a first orifice 20 of the backing plate 14. Moreover, according to certain embodiments, the aperture 46 may allow for light to pass, directly or indirectly, from the chamber 42 to the orifice 20 so that the light may be detected by the detector 32. As discussed below, the sample holder 38 may include a second aperture that is generally aligned with a second aperture 21 in the backing plate 14 when the adapter 10 is secured to the electronic device 12 that allows light emitted from the light emitter 34 of the hand held electronic device 12 to pass into the second aperture and subsequent (directly or indirectly) into the chamber 42.

Figure 6:
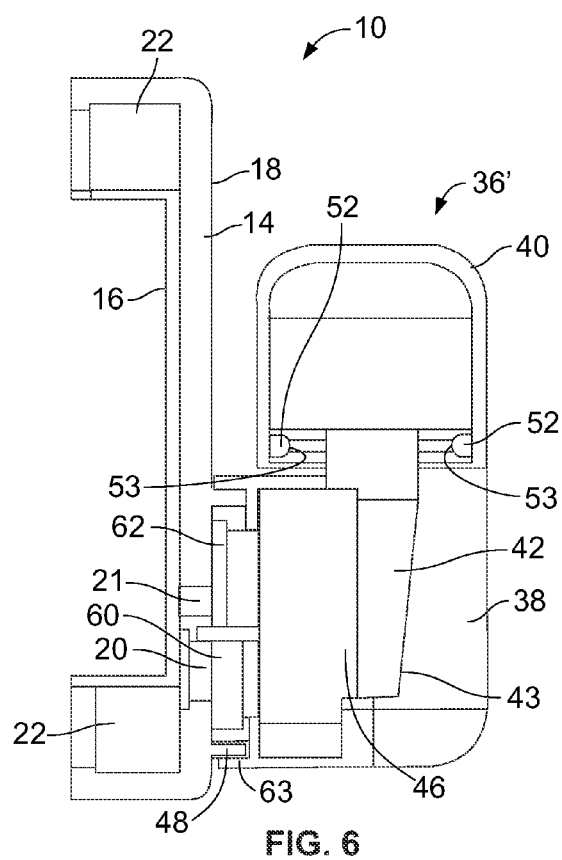
FIG. 6 is a cross sectional view of the adapter shown in FIG. 1 or 2 that have filters for filtering wavelengths of light delivered to the sample and filtering wavelengths of light detected by the detector.

Additionally, the first orifice 20 and second orifice 21 may include, or be operably connected to, one or more lenses or one or more light filters. For example, the first orifice 20 may include or be operably connected to a lens that assists in enhancing the focus and/or the detection of the light that is detected by the detector 32. According to certain embodiments, the lens may be a concave surface that concentrates the light that is detected by the detector 32. According to certain embodiments, the lens in the first orifice 20 may have a concave reflective surface that is configured to concentrate light being delivered to, and thus detected by, the detector 32. Alternatively, referencing FIG. 6, the first orifice 20 may include, or be operably connected to, a filter 60 that filters the wavelength of light that is delivered to the detector 32. As shown in FIG. 6, according to certain embodiments, rather than being located in the first orifice 20, the filter 60 may abut against or be adjacent to the second side 18 of the backing plate 14. The filter 60 may be operably secured to a portion of the projection 48, such as, for example, by a press fit or through the use of an adhesive. Further, the filter 60 may consist of more than one filter. Moreover, a plurality of filters 60 may be employed that filter different wavelengths of light.

Additionally, as shown in FIG. 6, the sample holder 38 may include a hub 63. According to certain embodiments, the hub 63 is configured to increase the distance between the chamber 42 and the backing plate 14 so as to improve the focus of the detector 32. Additionally, the hub 63 may provide an area for the placement of a lens that may improve the detection or concentration of the light detected by the detector 32. Additionally, or alternatively, the hub 63 may also provide an area for placement of the one more filters 60.

Similarly, the second orifice 21 may also include, or be operably connected to, a lens that may assist in directing light from the light emitter 34 toward the sample or other portion of the sample housing 36. Alternatively, referencing FIG. 6, the second orifice 21 may include or be operably connected to a filter 62 that filters the wavelength of light emitted from the light emitter 34 that will be delivered to the sample. Moreover, as light from the light emitter 34 is directed toward the sample, such a filter 62 may filter out wavelengths of light that are outside of a light wavelength used for excitation of the sample. Similar to the filter 60 of the first orifice 20, according to certain embodiments, the filter 62 for the second orifice 21 may also be operably secured to a portion of the projection 48 that extends from, or is operably connected to, the second side of the backing plate 14.

The sample holder 38 may be operably attached to the backing plate 14. For example, according to certain embodiments, the backing plate 14 may include one or more projections 48 that extend away from the second side 18 of the backing plate 14 that engage with one or more mating recesses 50 in the sample holder 38. Such a mating relationship between the projection(s) 48 and the recess(es) 50 may provide a friction or snap fit that secures the sample housing 30 to the backing plate 14. Additionally, or in lieu of a friction or snap fit, the sample holder 38 may be secured to the backing plate 14 by an adhesive or a plastic weld. According to other embodiments, the projection 48 and sample holder 38 may be secured to each other by a threaded engagement, such as, for example a male threaded portion of the projection 48 or other portion of the backing plate 14 that mates a female threaded portion of the sample holder 38, or vice versa. According to another embodiment, at least a portion of the sample holder 38 and the backing plate 14 may be a single, integral unit, such as being molded or otherwise formed together.

Figure 5:
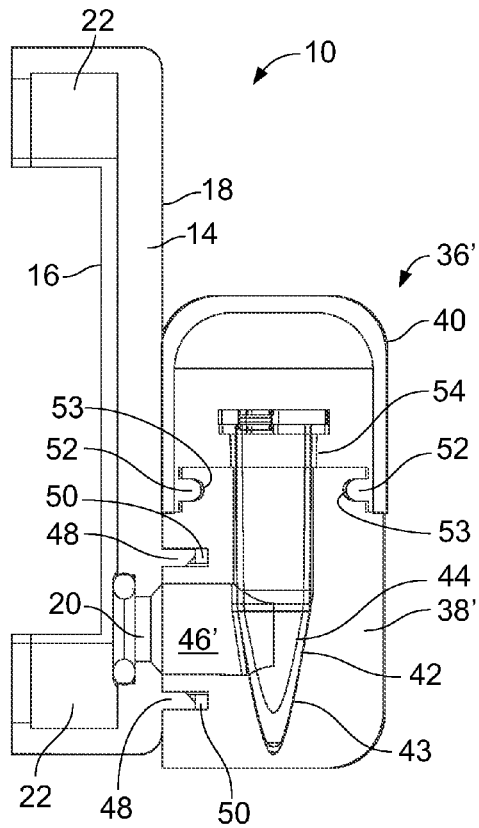
FIG. 5 is a side cross sectional view of the adapter illustrated in FIG. 1 or 2.

The cap 40 is configured to be moved between open and closed positions and vice versa. When in the open position, the cap 40 is positioned such that at least a portion of the sample and/or sample vessel 44 may be placed into, or removed from, the chamber 42. When the cap 40 is in a closed position, the cap 40 is secured to the sample holder 38 and prevents the entry or removal of the sample or sample vessel 44 into/out of the chamber 42. As shown in FIG. 5, according to certain embodiments, the cap 40 may also include a cavity 54 that is configured to be placed around at least a portion of the sample vessel 44 when the cap 40 is in the closed position.

Further, when in the closed position, the cap 40 securely engages the sample holder 38. For example, according to certain embodiments, the cap 40 may threadingly engage the sample holder 38. Alternatively, as shown in at least FIG. 5, when in a closed position, the cap 40 may be secured to the sample holder 38' of the sample housing 36' by use of a friction or snap fit. For example, the cap 40 may include one or more protrusions 52 that are received in one or more mating depressions 53 in the sample holder 38', or vice versa. According to certain embodiments, the cap 40 may be pivotally connected to the sample holder 38 by a hinge.

The adapter 10 may be constructed from a variety of different materials. For example, according to certain embodiments, the adapter 10 may be molded using polypropylene or polyethylene, among others. Additionally, the cap 40 and sample holder 38 may or may not form a single, integral piece. The sample holder 38 and cap 40 may also be opaque so as to prevent or limit undesirable external light from entering into the chamber 42. Additionally, according to certain embodiments, at least a portion of the sample holder 38, such as, for example, the chamber wall 43, may include or be connected to a reflective surface, such as, for example, a reflective paint or foil, that reflects light emitted from the sample and/or the light emitter.

Figure 7:
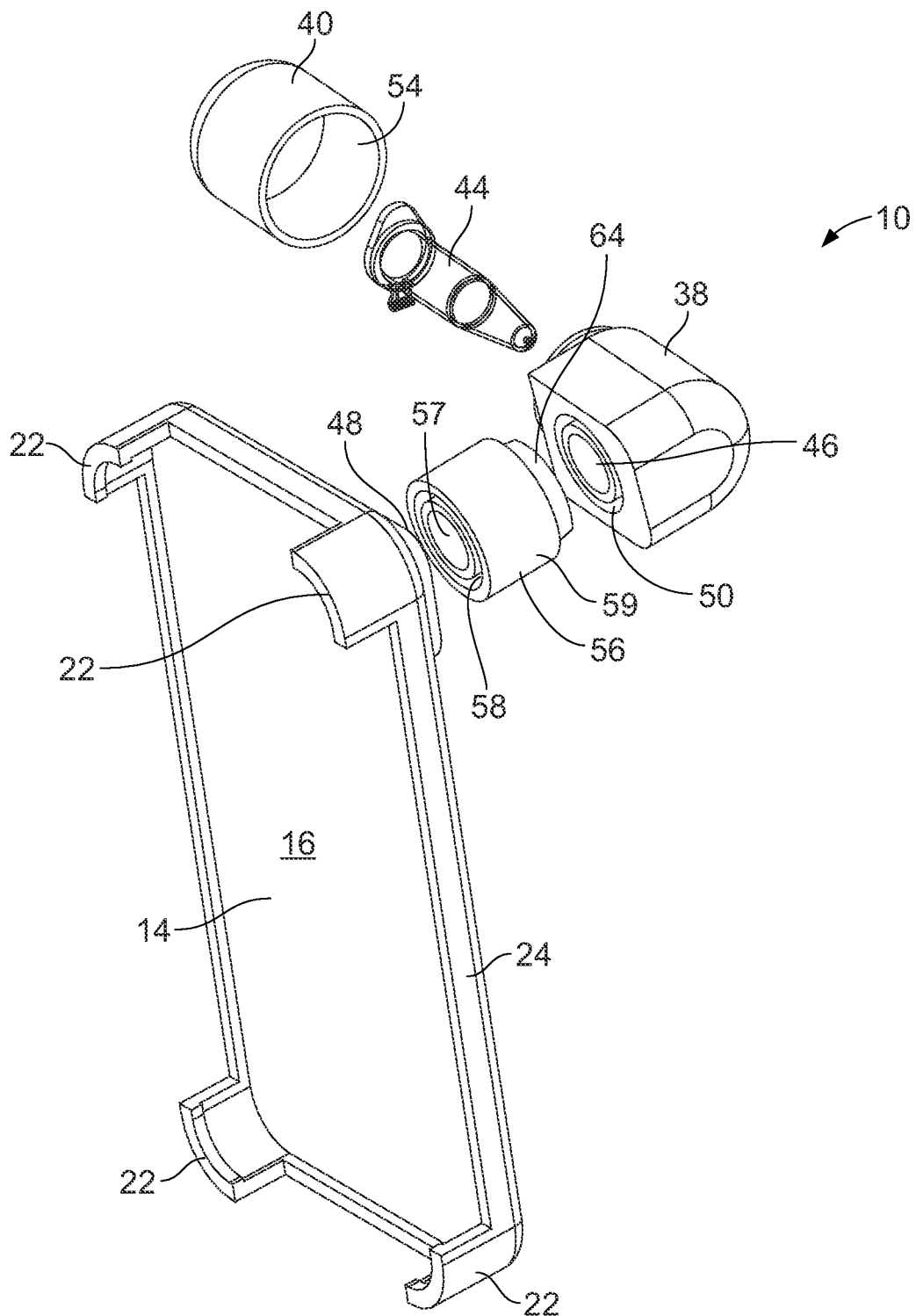
FIG. 7 illustrates an exploded view of an adapter that includes an extender, according to an embodiment of the present invention.
Figure 8:
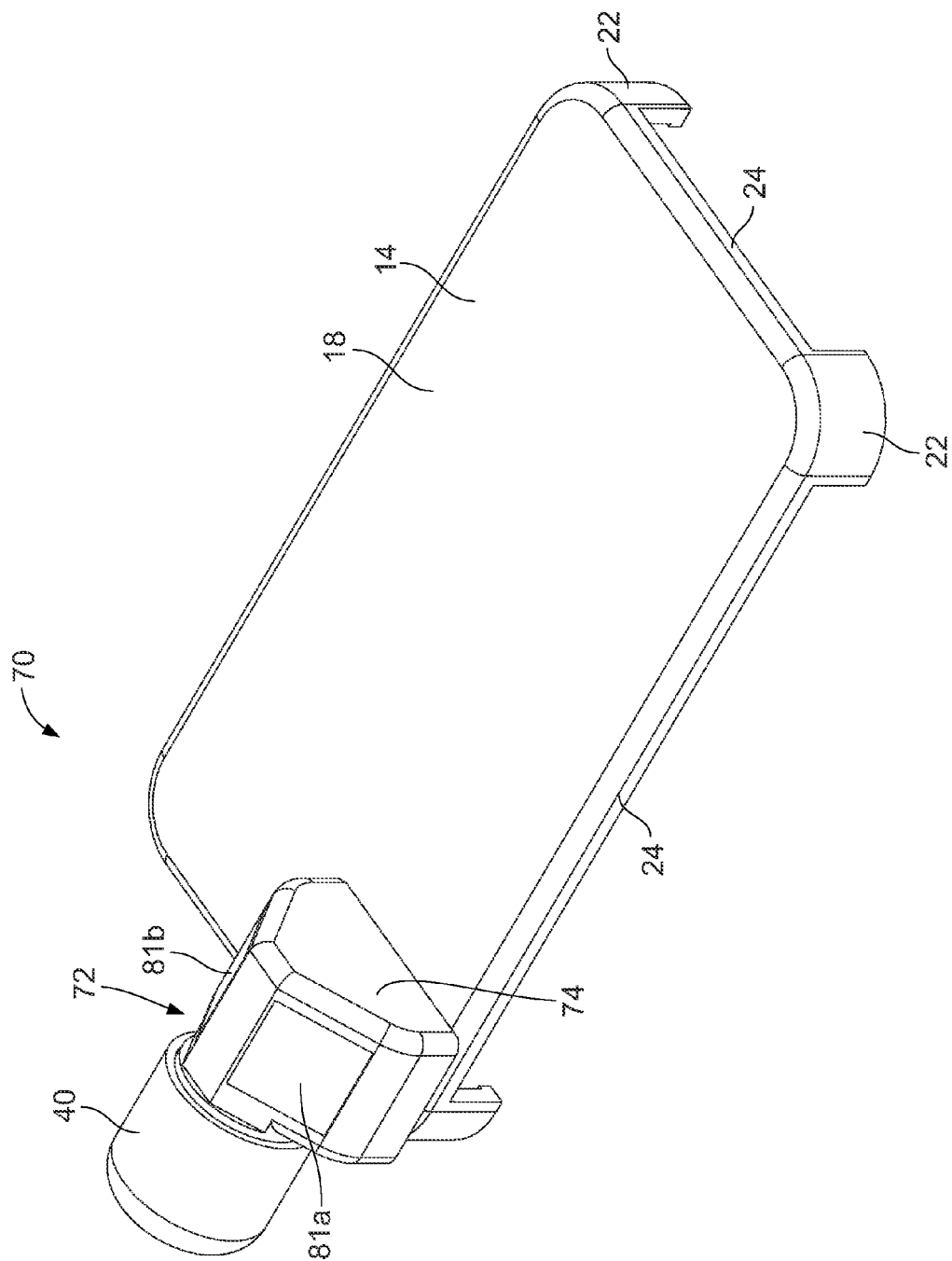
FIG. 8 illustrates a top perspective view of an adapter that is configured to be secured to a hand-held electronic device that is used to detect an optical property of a sample, according to an embodiment of the present invention.

FIG. 7 illustrates an exploded view of an adapter 10 that includes an extender 56, according to an embodiment of the present invention. The extender 56 may increase the distance between the detector 32 and the chamber 42 of the sample holder 38, and thereby increase the distance between the detector 32 and the sample and/or sample vessel 44 located in the chamber 42. Such an increase in distance may enhance the ability of the detector 32 to focus on the light emitted from or through the sample. Accordingly, the extender 56 includes a passage 57 that is in communication with the first and second orifices 20, 21 of the backing plate, as well as the aperture 46 of the sample holder 38.

Additionally, according to certain embodiments, the extender 56 may be used to house one or more lenses, such as, for example, in the passage 57, that assist with improving the focus of the detector 32 or concentration of the light that is detected by the detector 32. Further, in addition to, or in lieu a lens, the extender 56 may also include one or filters, such as filters 60 and 62, that filter a defined wavelength of light delivered to the sample from the light emitter 34 and/or one or more filters that filter a defined wavelength of the excitation light that is detected by the detector 32.

The extender 56 is operably secured to both the backing plate 14 and the sample holder 38. For example, according to certain embodiments, the extender 56 may be secured to the backing plate 14 by a friction fit between a recess 58 in the extender 56 and the projection 48 of the backing plate 14, or vice versa. Similarly, the sample holder 38 may be secured to the extender 56 by a friction fit between a hub 64 extending from an outer surface 59 of the extender 56 and the recess 50 of the sample holder 38.

FIGS. 8-11 illustrate another embodiment of an adapter 70 that is configured to be secured to a hand-held electronic device 12 having a detector 32 that is used to detect an optical property of a sample according to an embodiment of the present invention. As shown, the adapter 70 includes a sample holder 72 that includes a sample holder 74 and a cap 40. Similar to the adapter 10 discussed above, at least a portion of the adapter 70 may be integrally formed with the backing plate 14, or may be operably secured to the backing plate 14, such as, for example through a threaded or press fit engagement. Additionally, when in the closed position, the cap 40 securely engages the sample holder 74, such as, a threaded or press fit engagement between the cap 40 and an upper portion 76 of the sample holder 74. Further, according to certain embodiments, the sample holder 74 and cap 40 may be constructed from an opaque material so as to prevent exterior light from passing through the walls of the sample holder 74 and cap 40.

The sample holder 74 has a first aperture 75a that generally aligns with the first orifice 20 and a second aperture 75b that generally aligns with the second orifice 21. A divider 78 may separate at least a portion of the first and second apertures 75a, 75b and, more specifically, prevent light being emitted or received through one aperture 75b from being directly received in the other aperture 75a, and vice versa. Further, the sample holder 74 has at least one reflective surface 80a, 80b that is operably secured to the sample holder 74. In the illustrated embodiment, the at least one reflective surface 80a, 80b is part of an insert 81a, 81b that is operably secured to the sample holder 74. For example, the insert 81a, 81b may be secured to a window 82 in the sample holder 74, such as, for example, by a friction or snap fit, adhesive, and/or other locking engagement. The at least one reflective surface 80a, 80b of the insert 81a, 81b provides a higher degree of reflection or refraction, than the adapter housing 74. For example, according to certain embodiments, while the sample holder 74 may be constructed or molded from an opaque plastic, the reflective surface 80a, 80b may be a mirror. However, similar to the sample holder 74, the insert 81a, 81b is also constructed to prevent external light outside of the sample housing 72 from passing through the insert 81a, 81b and into the respective aperture 75a, 75b. Further, according to the illustrated embodiment, a wall 73a, 73b of the sample holder 74 in may oriented such that the insert 81a, 81b that is secured to that wall 73a, 73b is oriented, such as angled, so that the associated reflective surface 80a, 80b may generally re-direct reflected or refracted light in a desired direction. For example, as shown in at least FIGS. 8-10, walls 73a, 73b of the sample holder 74 are angled such that the reflective surfaces 80a, 80b may re-direct and/or reflect light toward the chamber 42 or the detector 32, respectively.

Figure 9:
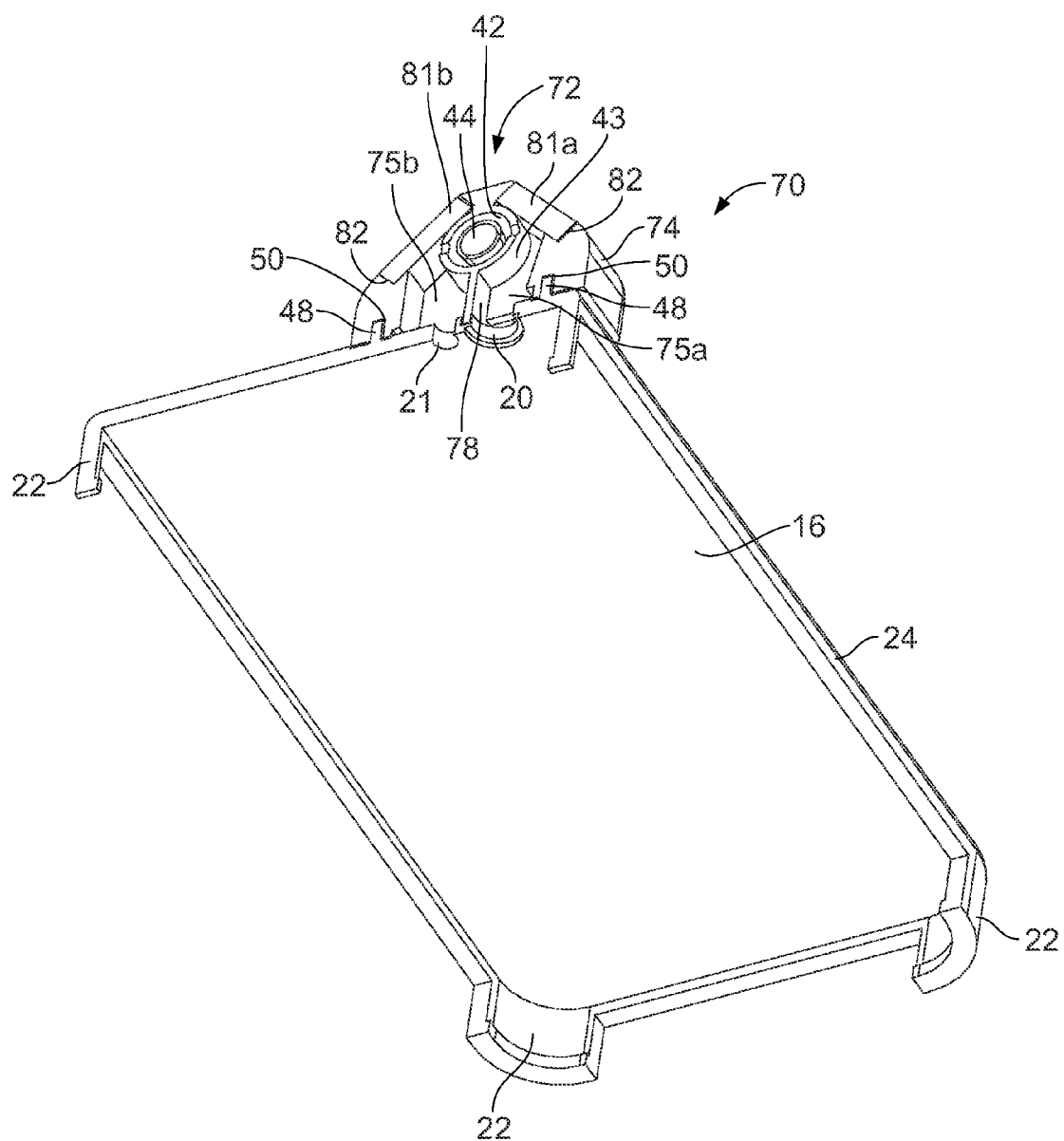
FIG. 9 illustrates a partial cross sectional, bottom perspective view of the adapter illustrated in FIG. 8.
Figure 10:
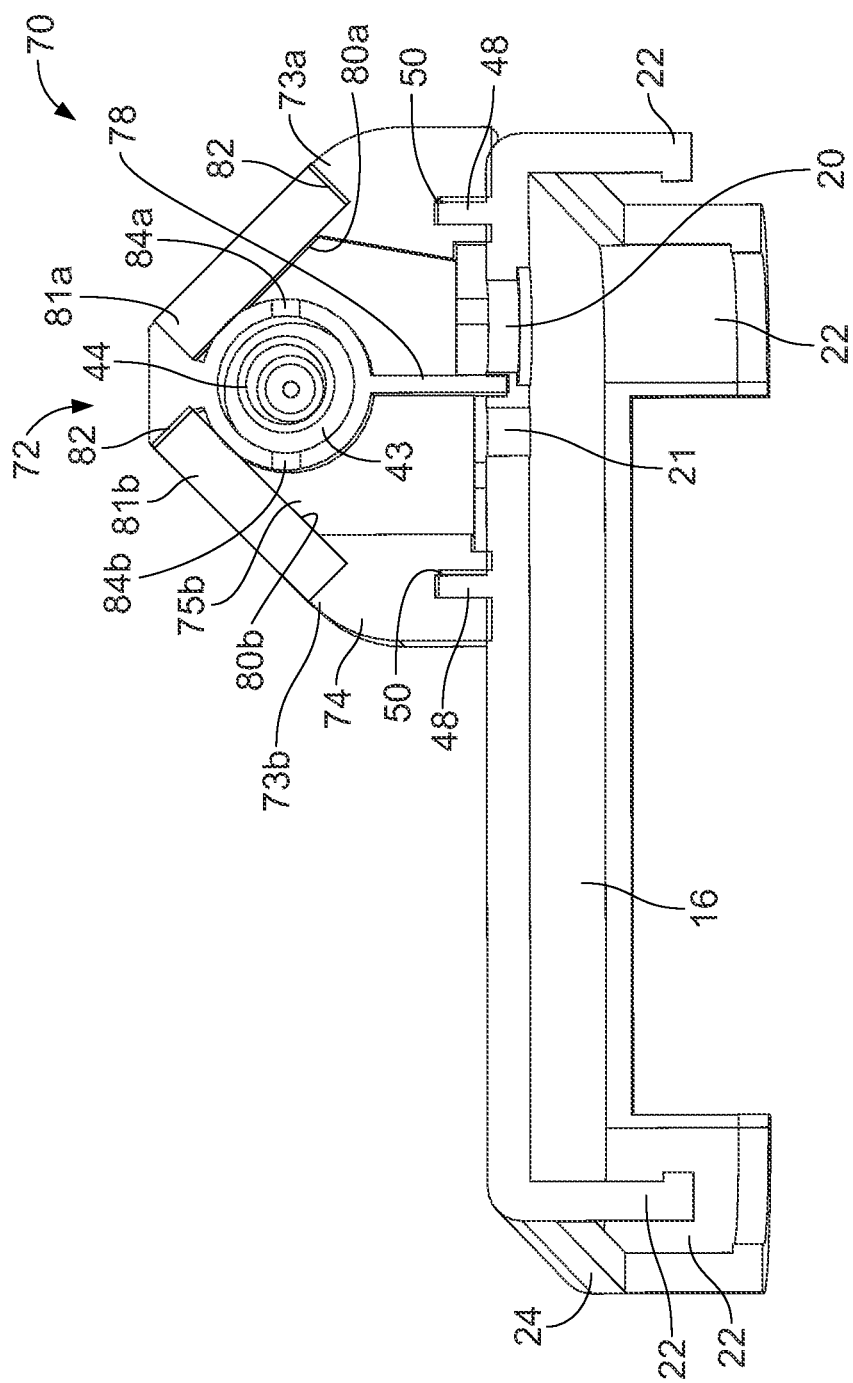
FIG. 10 illustrates a partial cross sectional, front perspective view of the adapter illustrated in FIG. 8.
Figure 11:
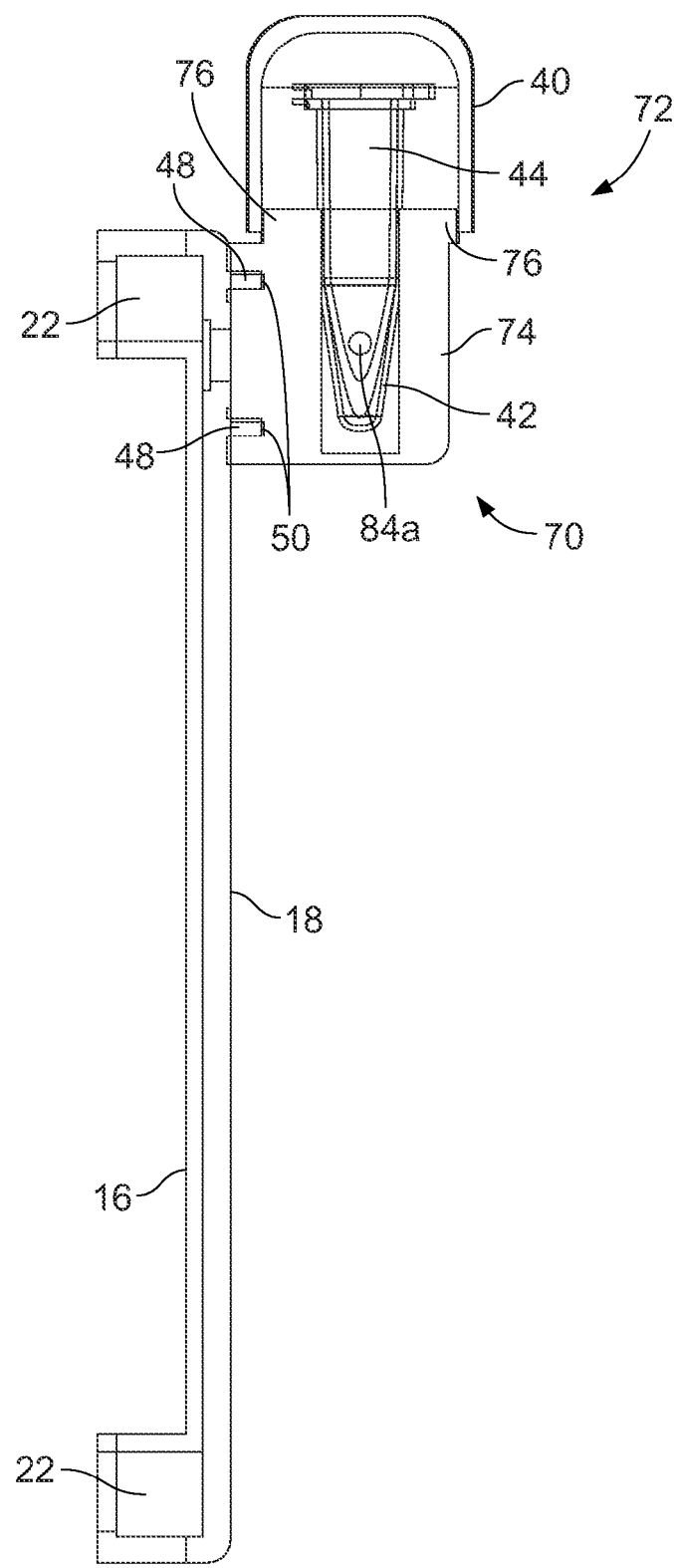
FIG. 11 illustrates a side cross sectional view of the adapter illustrated in FIG. 8.
Figure 12:
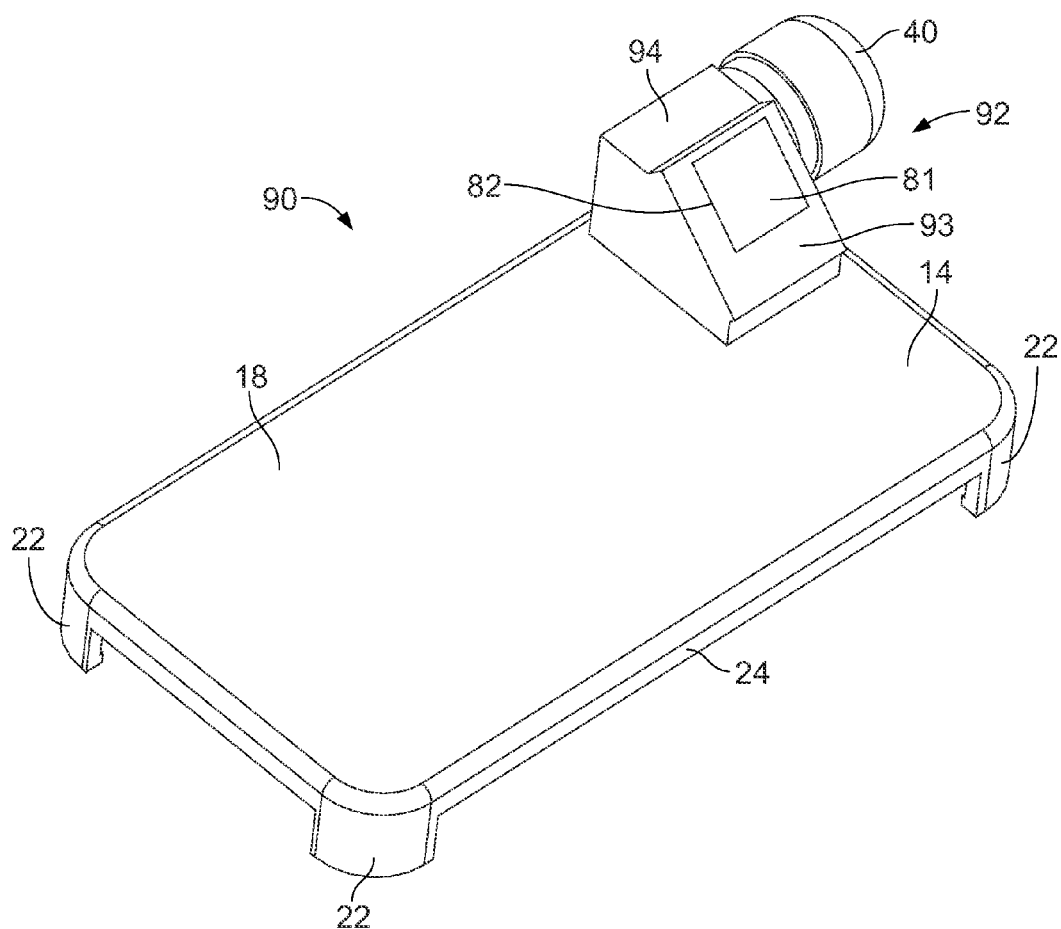
FIG. 12 illustrates a perspective view of an adapter that is configured to be secured to a hand-held electronic device that is used to detect an optical property of a sample, according to an embodiment of the present invention.
Figure 13:
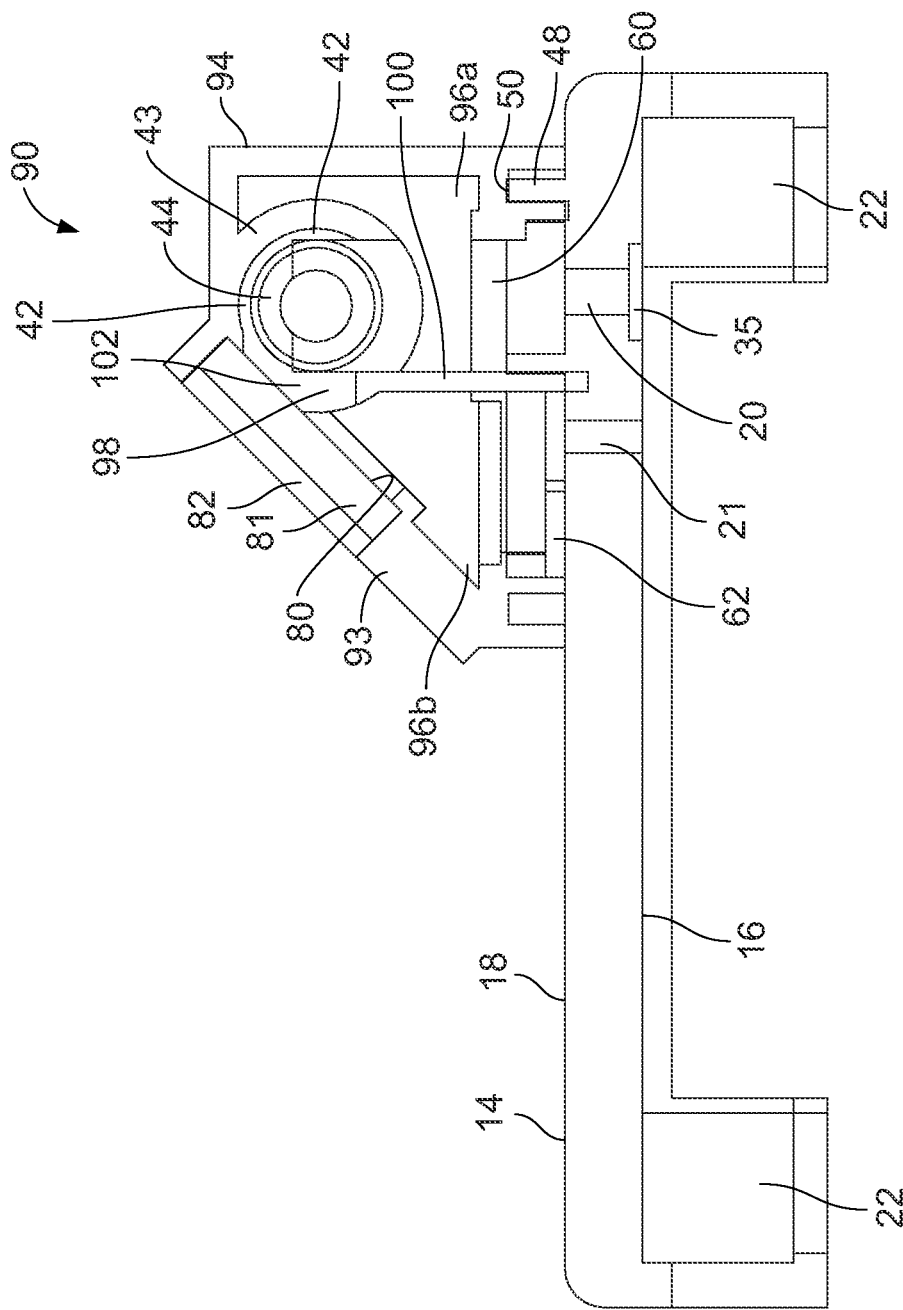
FIG. 13 illustrates a top cross sectional view of the adapter illustrated in FIG. 12.
Figure 14:
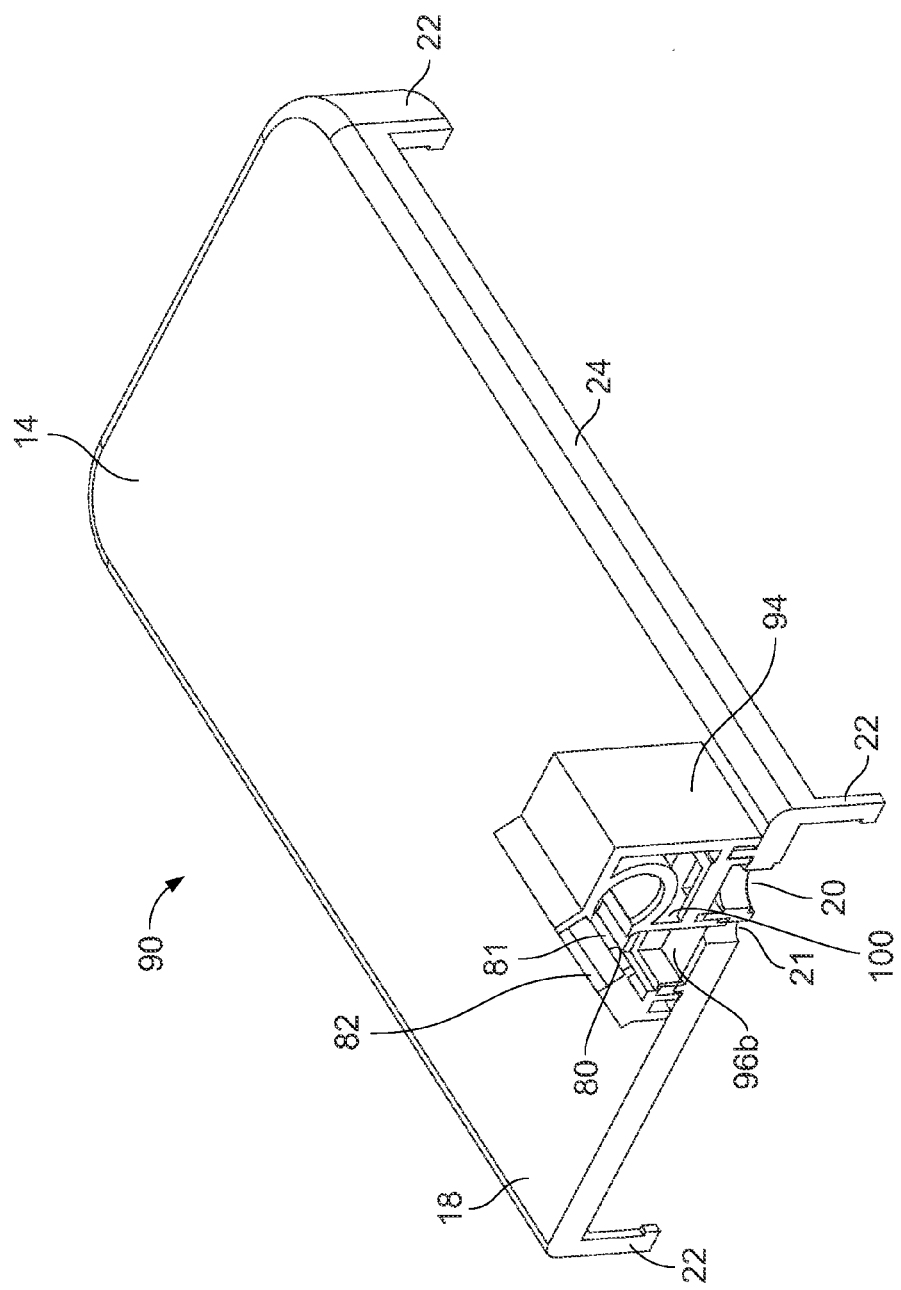
FIG. 14 illustrates a partial cross sectional, side perspective view of the adapter illustrated in FIG. 12.

As shown in FIGS. 9-11, the first and second apertures 75a, 75b may be separated from the chamber 42 by at least a portion of the chamber wall 43. Further, the chamber wall 43 may include a pair of openings 84a, 84b that allow light to be transmitted into and/or out of the chamber 42. Accordingly, a portion of the chamber 42 may be in communication with the first aperture 75a via a first opening 84a, while a portion of the chamber 42 may be in communication with the second aperture 75b via a second opening 84b.

During use, an adapter 70 having first and second reflective surfaces 80a, 80b may be operably secured to a hand-held electronic device 12 such as by the engagement of the integral surface(s) 22 with the edge 26 of the hand-held electronic device 12. Such an engagement also permits the first orifice 20 to be generally aligned with the detector 32 of the device 12. Additionally, such engagement also allows the second orifice 21 of the adapter 70 to generally align with the light emitter 34 of the device 12. The user may then operate the hand-held electronic device 12 so that a light is emitted from the light emitter 34 of the hand-held electronic device 12. The light emitted from the device 12 may then pass through the second aperture 75b and to the second reflective surface 80b. The second reflective surface 80b may be positioned so as to reflect at least a portion of the emitted light toward the second opening 84b in the chamber wall 43. At least a portion of the reflective light may then reach the chamber 42, wherein at least a portion of the light may pass to and/or through a sample contained in the chamber 42 and/or contained in a sample vessel 44 in the chamber 44. Light passing through and/or being emitted from the sample, such as excitation light, may then pass through the first opening 84 in the chamber wall 43. Light that has passed through the first opening 84 may then enter the first aperture 75a, where the light may travel to the first reflective surface 80a. The first reflective surface 80a may then reflect the light toward the first orifice 20 so that at least a portion of the reflected or refracted light is detected by the detector 32.

The light, image, or other data that is detected by the detector 32 may then be recorded by the device 12 and/or transferred/downloaded from the device 12. Moreover, the detected light, image, and/or data detected by the detector 32 may be analyzed using programming stored on the device 12 and/or be transferred to another microprocessor based device for a variety of different purposes, including analysis and recording, among other purposes or uses. For example, the hand-held electronic device 12, and more specifically, the detector 32, may take a picture that could then be evaluated for light measured above a threshold value. Such evaluation may involve software or applications on the device 12 or on another, external processor based device. For example, if the sample was being measured with native or recombinant, wild-type or mutant luciferase, the green portion of the photo can be analyzed. Additionally, the entire image obtained by the camera of the device 12, or a portion of that image, such as a region of interest, may be evaluated. Further, summing pixel values over the entire image or a region of interest in the image could provide a numerical value that is used for comparisons with the numerical values of samples having known properties or for other evaluation purposes. Such numerical values may also be adjusted, if necessary or desired, to compensate for background light. For example, the summed pixel value may be adjusted by subtracting a color detected by the detector 32 that was not produced by the reaction between the sample and the reactant, such as, for example, the blue values of the pixels. By fitting the measured value into a standard curve, the concentration of a target substance in the sample may be derived.

FIGS. 12-15 illustrate another embodiment of an adapter 90 that is configured to be secured to a hand-held electronic device 12 having a detector 32 that is used to detect an optical property of a sample according to an embodiment of the present invention. The adapter 90 has a sample holder 92 that includes a sample holder 94 and a cap 40. Similar to the adapters 10, 70 discussed above, at least a portion of the adapter 90 may be integrally formed with the backing plate 14 or may be operably secured to the backing plate 14, such as, for example, through a threaded, friction, or snap fit engagement. Further, the sample holder 94 may also be constructed from an opaque material so as to prevent or limit exterior light from passing through the walls of the sample holder 94.

The sample holder 94 includes a first aperture 96a, second aperture 96b, and a reflective surface 80. According to certain embodiments, the sample holder 94 may also include one or more filters 60, 62 that filter certain, predetermined light wavelengths. Similar to the reflective surfaces 80a, 80b previously discussed with respect to FIGS. 12-15, the reflective surface 80 shown in FIGS. 13-15 has a higher degree of reflectivity than the material of the sample holder 94. Additionally, as also shown in at least FIGS. 13-15, the reflective surface 80 may be part of an insert 81 that is operably secured in a window 82 along a wall 93 of the sample holder 94.

Figure 15:
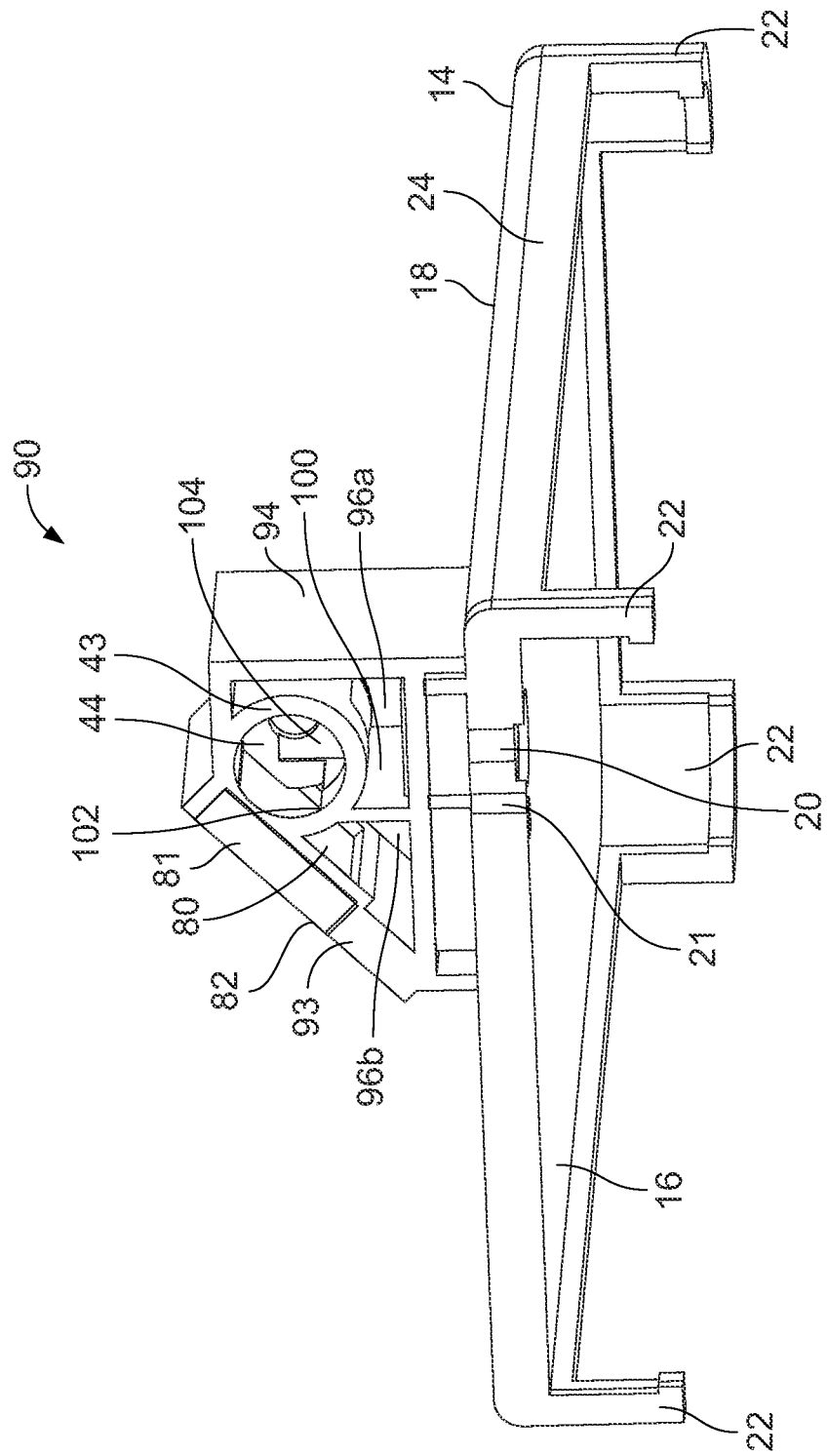
FIG. 15 illustrates a top cross sectional, perspective view of the adapter illustrated in FIG. 12.
Figure 16:
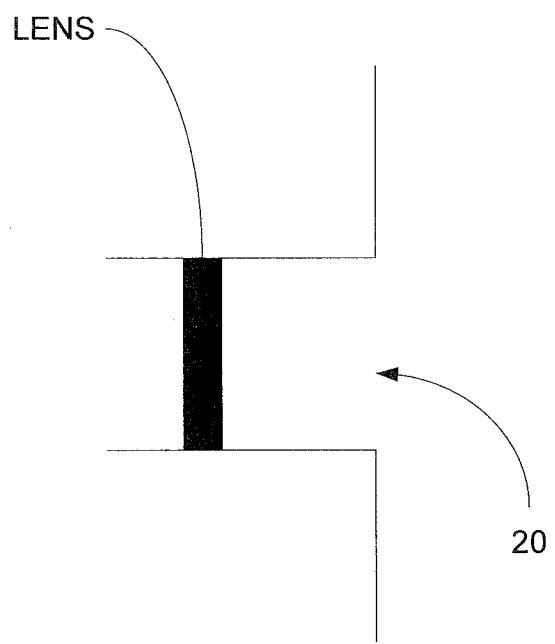
FIG. 16 illustrates an embodiment of an orifice that includes a lens.

The sample holder 94 includes both a first aperture 96a that generally aligns with the first orifice 20 in the backing plate 14 and a second aperture 96b that generally aligns with the second orifice 21. A divider 100 separates at least a portion of the first and second apertures 96a, 96b, and more specifically prevents light being emitted or received through one aperture 96b from being directly passing into the other aperture 96a, and vice versa. A distal end 98 of the divider 100 includes an orifice 102 between a portion of the divider 100 and the reflective surface 80 and/or the sample holder 94 that is configured to allow light to pass from the second aperture 96b and into the chamber 42 of the sample holder 94. Additionally, the chamber wall 43 includes an opening or orifice 104 that allows light to pass from the chamber 42, or the sample contained therein, to the first aperture 96a. As shown in FIG. 15, the orifice 104 in the chamber wall 43 is generally aligned with the first orifice 20 in the backing plate 14.

During use, the light emitter 34 of the hand-held electronic device 12 may be activated so that a light is transmitted through the second orifice 21 in the backing plate 14 and into the second aperture 96b. This light may then travel to the insert 81, where the light is reflected or refracted by the reflective surface 80 toward the chamber 42. As illustrated in the embodiment shown in FIGS. 12-15, the wall 93 containing the insert 81 may be angled so that the reflective surface 80 re-directs the path of the light toward the chamber 42. At least a portion of the reflected or refracted light may then pass through the orifice 102 in the divider 100 before reaching the chamber 42 and the sample contained therein (or contained in a sample vessel 44 positioned in the chamber 42). As at least a portion of the chamber 42 is in communication with the detector 32 via the first orifice 20 in the backing plate 14, the first aperture 96a, and the orifice 104 in the chamber wall 43, the detector 32 of the hand-held electronic device 12 may be able to receive light passing through or being emitted from the sample. As previously discussed, the detection of such light, image, and/or the corresponding data may then be used by the device 12 for analysis of the optical properties of the sample, as discussed above, and/or may otherwise be transferred to another processor based device for a variety of different purposes or uses, such as analysis and recording, among others.

The invention claimed is:

1. An adapter for use with a hand-held consumer electronic device, the hand-held consumer electronic device having a detector and an imaging device for detecting one or more properties of a sample, the adapter comprising:
a backing plate having at least one orifice and at least one integral surface, the at least one integral surface being configured to engage at least a portion of an outer surface of the hand-held consumer electronic device to secure the adapter to the hand-held consumer electronic device, the backing plate configured to be adjacent to at least a portion of the outer surface of the hand-held consumer electronic device when the adapter is secured to the hand-held consumer electronic device, at least one of the at least one orifices being positioned along the backing plate so as to generally align with the detector when the adapter is secured to the hand-held consumer electronic device;
a sample holder operably secured to the backing plate, the sample holder having an aperture and a chamber, the aperture being in communication with at least a portion of a chamber, the chamber configured to receive the placement of at least a portion of the sample or a sample vessel, the aperture configured to generally align with the detector and at least one of the at least one orifice when the adapter is secured to the hand-held consumer electronic device; and
a cap configured to engage the sample holder, the cap configured to cover at least a portion of the chamber or the sample vessel when the cap is engaged in a closed position with the sample holder,
wherein the adapter further includes an activatable light-emitting diode, the light emitting diode configured to emit light at least through the aperture of the sample holder,
wherein the at least one orifice has a first orifice and a second orifice, the first orifice configured to generally align with the detector, and the second orifice configured to generally align with a light emitter of the hand-held consumer electronic device, and
wherein the first orifice includes at least one lens configured to enhance the optical detection of the detector.

2. An adapter for use with a hand-held consumer electronic device, the hand-held consumer electronic device having a detector and an imaging device for detecting one or more properties of a sample, the adapter comprising:
a backing plate having at least one orifice and at least one integral surface, the at least one integral surface being configured to engage at least a portion of an outer surface of the hand-held consumer electronic device to secure the adapter to the hand-held consumer electronic device, the backing plate configured to be adjacent to at least a portion of the outer surface of the hand-held consumer electronic device when the adapter is secured to the hand-held consumer electronic device, at least one of the at least one orifices being positioned along the backing plate so as to generally align with the detector when the adapter is secured to the hand-held consumer electronic device;
a sample holder operably secured to the backing plate, the sample holder having an aperture and a chamber, the aperture being in communication with at least a portion of a chamber, the chamber configured to receive the placement of at least a portion of the sample or a sample vessel, the aperture configured to generally align with the detector and at least one of the at least one orifice when the adapter is secured to the hand-held consumer electronic device; and
a cap configured to engage the sample holder, the cap configured to cover at least a portion of the chamber or the sample vessel when the cap is engaged in a closed position with the sample holder, wherein the adapter further includes an activatable light-emitting diode, the light emitting diode configured to emit light at least through the aperture of the sample holder, wherein the at least one orifice has a first orifice and a second orifice, the first orifice configured to generally align with the detector, and the second orifice configured to generally align with a light emitter of the hand-held consumer electronic device, and wherein the first orifice includes a concave reflective surface configured to concentrate light being detected by the detector.

3. An adapter for use with a hand-held consumer electronic device, the hand-held consumer electronic device having a detector and an imaging device for detecting one or more properties of a sample, the adapter comprising:

a backing plate having at least one orifice and at least one integral surface, the at least one integral surface being configured to engage at least a portion of an outer surface of the hand-held consumer electronic device to secure the adapter to the hand-held consumer electronic device, the backing plate configured to be adjacent to least a portion of the outer surface of the hand-held consumer electronic device when the adapter is secured to the hand-held consumer electronic device, at least one of the at least one orifices being positioned along the backing plate so as to generally align with the detector when the adapter is secured to the hand-held consumer electronic device;

a sample holder operably secured to the backing plate, the sample holder having an aperture and a chamber, the aperture being in communication with at least a portion of a chamber, the chamber configured to receive the placement of at least a portion of the sample or a sample vessel, the aperture configured to generally align with the detector and at least one of the at least one orifice when the adapter is secured to the hand-held consumer electronic device; and a cap configured to engage the sample holder, the cap configured to cover at least a portion of the chamber or the sample vessel when the cap is engaged in a closed position with the sample holder, wherein the adapter further includes an activatable light-emitting diode, the light emitting diode configured to emit light at least through the aperture of the sample holder, and wherein the adapter further includes a first filter positioned between the light emitter and the chamber, the first filter configured to filter a defined wavelength range of light emitted from the light emitter.

4. An adapter for use with a hand-held consumer electronic device, the hand-held consumer electronic device having a detector and an imaging device for detecting one or more properties of a sample, the adapter comprising:

a backing plate having at least one orifice and at least one integral surface, the at least one integral surface being configured to engage at least a portion of an outer surface of the hand-held consumer electronic device to secure the adapter to the hand-held consumer electronic device, the backing plate configured to be adjacent to least a portion of the outer surface of the hand-held consumer electronic device when the adapter is secured to the hand-held consumer electronic device, at least one of the at least one orifices being positioned along the backing plate so as to generally align with the detector when the adapter is secured to the hand-held consumer electronic device;

a sample holder operably secured to the backing plate, the sample holder having an aperture and a chamber, the aperture being in communication with at least a portion of a chamber, the chamber configured to receive the placement of at least a portion of the sample or a sample vessel, the aperture configured to generally align with the detector and at least one of the at least one orifice when the adapter is secured to the hand-held consumer electronic device; and a cap configured to engage the sample holder, the cap configured to cover at least a portion of the chamber or the sample vessel when the cap is engaged in a closed position with the sample holder, wherein the adapter further includes an extender positioned between the backing plate and the sample holder, the extender having a passage and an outer surface, the passage being generally aligned with the first orifice and the aperture.

5. The adapter of claim 4, wherein the sample holder further includes a reflective surface configured to reflect light toward the chamber.

6. The adapter of claim 4, wherein the adapter further includes an activatable light-emitting diode, the light emitting diode configured to emit light at least through the aperture of the sample holder.

7. The adapter of claim 6, wherein the at least one orifice has a first orifice and a second orifice, the first orifice configured to generally align with the detector, and the second orifice configured to generally align with a light emitter of the hand-held consumer electronic device.

8. An adapter for use with a hand-held consumer electronic device, the hand-held consumer electronic device having a detector and an imaging device for detecting one or more properties of a sample, the adapter comprising:

a backing plate having at least one orifice and at least one integral surface, the at least one integral surface being configured to engage at least a portion of an outer surface of the hand-held consumer electronic device to secure the adapter to the hand-held consumer electronic device, the backing plate configured to be adjacent to least a portion of the outer surface of the hand-held consumer electronic device when the adapter is secured to the hand-held consumer electronic device, at least one of the at least one orifices being positioned along the backing plate so as to generally align with the detector when the adapter is secured to the hand-held consumer electronic device;

a sample holder operably secured to the backing plate, the sample holder having an aperture and a chamber, the aperture being in communication with at least a portion of a chamber, the chamber configured to receive the placement of at least a portion of the sample or a sample vessel, the aperture configured to generally align with the detector and at least one of the at least one orifice when the adapter is secured to the hand-held consumer electronic device; and a cap configured to engage the sample holder, the cap configured to cover at least a portion of the chamber or the sample vessel when the cap is engaged in a closed position with the sample holder, wherein the sample holder further includes a reflective surface configured to reflect light toward the chamber, and wherein the sample holder further includes a first filter positioned between the light emitter and the reflective surface, the first filter configured to filter a defined wavelength range of light emitted from the light emitter.

9. The adapter of claim 8, further including a second filter positioned between the chamber and the detector, the second filter configured to filter excitation or emission light.

10. An adapter for use with a hand-held consumer electronic device, the hand-held consumer electronic device having a detector and an imaging device for detecting one or more properties of a sample, the adapter comprising:
- a backing plate having at least one orifice and at least one integral surface, the at least one integral surface being configured to engage at least a portion of an outer surface of the hand-held consumer electronic device to secure the adapter to the hand-held consumer electronic device, the backing plate configured to be adjacent to least a portion of the outer surface of the hand-held consumer electronic device when the adapter is secured to the hand-held consumer electronic device, at least one of the at least one orifices being positioned along the backing plate so as to generally align with the detector when the adapter is secured to the hand-held consumer electronic device;
- a sample holder operably secured to the backing plate, the sample holder having an aperture and a chamber, the aperture being in communication with at least a portion of a chamber, the chamber configured to receive the placement of at least a portion of the sample or a sample vessel, the aperture configured to generally align with the detector and at least one of the at least one orifice when the adapter is secured to the hand-held consumer electronic device; and
- a cap configured to engage the sample holder, the cap configured to cover at least a portion of the chamber or the sample vessel when the cap is engaged in a closed position with the sample holder, wherein the sample holder is opaque so as to block external light.

11. The adapter of claim 10, wherein the at least one integral surface comprises at least two integral arms.

12. An adapter for use with a hand-held consumer electronic device, the hand-held consumer electronic device having a detector and an imaging device for detecting one or more properties of a sample, the adapter comprising:
- a backing plate having at least one orifice and at least one integral surface, the at least one integral surface being configured to engage at least a portion of an outer surface of the hand-held consumer electronic device to secure the adapter to the hand-held consumer electronic device, the backing plate configured to be adjacent to least a portion of the outer surface of the hand-held consumer electronic device when the adapter is secured to the hand-held consumer electronic device, at least one of the at least one orifices being positioned along the backing plate so as to generally align with the detector when the adapter is secured to the hand-held consumer electronic device;
- a sample holder operably secured to the backing plate, the sample holder having an aperture and a chamber, the aperture being in communication with at least a portion of a chamber, the chamber configured to receive the placement of at least a portion of the sample or a sample vessel, the aperture configured to generally align with the detector and at least one of the at least one orifice when the adapter is secured to the hand-held consumer electronic device; and
- a cap configured to engage the sample holder, the cap configured to cover at least a portion of the chamber or the sample vessel when the cap is engaged in a closed position with the sample holder, wherein the sample holder includes a reflective foil or reflective paint configured to reflect light toward the detector.

* * * * *